United States Patent [19]

Maruyama et al.

[11] 4,230,706
[45] Oct. 28, 1980

[54] ANTIHYPERTENSIVE QUINAZOLINE COMPOUNDS

[75] Inventors: Isamu Maruyama, Minoo; Shunji Aono; Junki Katsube, both of Toyonaka, all of Japan

[73] Assignee: Sumitomo Chemical Company, Limited, Osaka, Japan

[21] Appl. No.: 21,776

[22] Filed: Mar. 19, 1979

[30] Foreign Application Priority Data

Mar. 29, 1978 [JP] Japan .................................. 53-37141

[51] Int. Cl.³ ............................................ A61K 31/505
[52] U.S. Cl. ...................................... 424/251; 544/291
[58] Field of Search .......................... 544/291; 424/251

[56] References Cited
U.S. PATENT DOCUMENTS 4,060,615  11/1977  Matier et al. ........................ 544/291

Primary Examiner—Paul M. Coughlan, Jr.
Attorney, Agent, or Firm—Stevens, Davis, Miller & Mosher

[57] ABSTRACT

Quinazoline compounds of the formula:

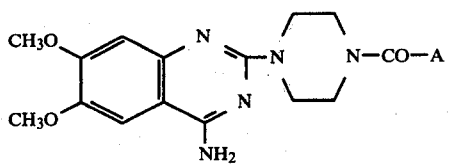

wherein A is

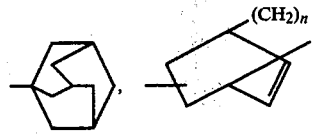

wherein n is an integer of 1 or 2, or

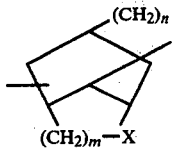

wherein X is O or $CH_2$, and n and m are independently an integer of 1 or 2, and its non-toxic pharmaceutically acceptable salts, having an excellent antihypertensive activity without causing adverse effects such as orthostatic hypotension.

9 Claims, No Drawings

ANTIHYPERTENSIVE QUINAZOLINE COMPOUNDS

The present invention relates to novel antihypertensive quinazoline compounds and to their preparation and use. More particularly, the invention relates to quinazoline compounds and their non-toxic pharmaceutically acceptable salts, which have now been found to have excellent antihypertensive properties and are useful for the treatment of hypertensive patients, to a pharmaceutical composition containing them, and to their preparation and use.

It is known that certain quinazoline derivatives are effective in reducing blood pressure of hypertensive patients (U.S. Pat. No. 3,511,836). In particular, Parzosin, 2-[4-(2-furoyl)-1-piperazinyl]-4-amino-6,7-dimethoxyquinazoline has been used for the treatment of hypertensive or congestive heart failure patients in certain countries including U.S.A. It is reported, however, that Prazosin tends to cause orthostatic hypotension in patients. Such undesirable temporary hypotension is said to be attributable to the potent α-adrenagic receptor blocking activity of Prazosin.

As the result of a study, it has now been found that the quinazoline compounds of the formula (I) mentioned below have an excellent antihypertensive activity and are useful for the treatment of hypertension. On experiments in normotensive and spontaneously hypertensive rats, the compounds of the present invention were found to have a potent long acting antihypertensive activity by oral administration. Unlike Prazosin, the compounds of the present invention exert a relaxing or spasmolytic effect on the smooth muscle of blood vessels, and its α-adrenagic receptor blocking activity is relatively weak in comparison with its potent hypotensive activity. So they exhibit characteristically a long acting antihypertensive effect without causing adverse effects such as orthostatic hypotension. Thus, the compounds of the present invention can conveniently be used for the treatment of hypertensive patients with essential hypertension and renal hypertension.

The quinazoline compounds of the present invention are represented by the formula:

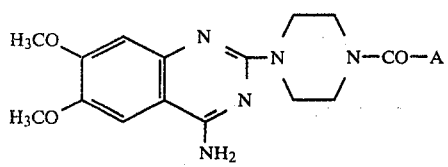

[I]

wherein A is

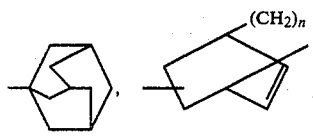

wherein n is an integer of 1 or 2, or

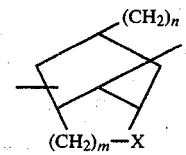

wherein X is O or $CH_2$, and n and m are independently an integer of 1 or 2.

In a preferred aspect, the present invention provides the following compounds:

2-{4-(1-Adamantanecarbonyl)-1-piperazinyl}-4-amino-6,7-dimethoxyquinazoline

4-Amino-6,7-dimethoxy-2-[4-{3-oxatricyclo[4,2,1,0$^{4,8}$]nonane-1-carbonyl}-1-piperazinyl]quinazoline 4-Amino-6,7-dimethoxy-2-[4-{3-oxatricyclo[4,3,1,0$^{4,9}$]decane-1-carbonyl}-1-piperazinyl]quinazoline 4-Amino-6,7-dimethoxy-2-[4-{3-oxatricyclo[4,2,1,0$^{4,8}$]nonane-9-carbonyl}-1-piperazinyl]quinazoline 4-Amino-2-[4-{bicyclo[2,2,1]hept-2-ene-5-carbonyl}-1-piperazinyl]-6,7-dimethoxyquinazoline 4-Amino-6,7-dimethoxy-2-[4-{4-oxatricyclo[5,2,1,0$^{5,9}$]decane-1-carbonyl}-1-piperazinyl]quinazoline 4-Amino-6,7-dimethoxy-2-[4-{tricyclo[4,2,1,0$^{4,8}$]nonane-1-carbonyl}-1-piperazinyl]quinazoline 4-Amino-6,7-dimethoxy-2-[4-{tricyclo[5,2,1,0$^{5,9}$]decane-1-carbonyl}-1-piperazinyl]quinazoline 4-Amino-6,7-dimethoxy-2-[4-{4-oxatricyclo[5,3,1,0$^{5,1}$0]undecane-1-carbonyl}-1-piperazinyl]quinazoline 4-Amino-2-[4-{bicyclo[2,2,2]oct-2-ene-5-carbonyl}-1-piperazinyl]-6,7-dimethoxyquinazoline The compounds of the present invention may be prepared by using conventional processes. For instance, they can be prepared by reacting a compound of the formula:

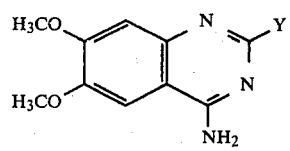

[II]

wherein Y is an halogen atom or an alkylthio group, with a compound of the formula;

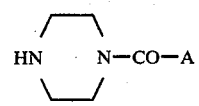

[III]

wherein A is as defined above.

With respect to the compounds of the formula [II], the halogen atom for Y may preferably be chlorine or bromine, and the alkylthio group for Y may preferably be methylthio or ethylthio. This reaction can be carried out in a suitable inert organic solvent at a temperature ranging from 0° C. to a boiling point of the solvent used. As the solvent used in this reaction, there may be exemplified benzene, toluene, xylene, dimethylformamide, pyridine, methanol, ethanol, propanol, butanol, pentanol and a mixture thereof.

The compounds of the present invention may also be prepared by reacting a compound of the formula;

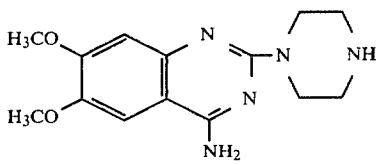

with a compound of the formula;

A—COOH [V]

wherein A is as defined above, or its reactive derivatives in an inert organic solvent.

As the reactive derivatives of the compounds of the formula [V], there may be exemplified acid halides (e.g., chloride, bromide), mixed acid anhydrides with lower alkoxycarbonyl halides (e.g., ethyl chloroformate, isobutyl chloroformate), or lower aliphatic carboxylic acids (e.g., pivaloyl acid), active esters (e.g., o-nitrophenyl ester, N-hydroxysuccinimide ester, N-hydroxydiphthalimide ester, hydroxybenzotriazole ester), and the like.

When the compounds of the formula [V] are used in the form of a free acid, the reaction may preferably be carried out in the presence of a coupling reagent such as N,N'-dicyclohexylcarbodiimide, N-cyclohexyl-N'-morpholinoethylcarbodiimide, triphenylphosphine and the like. The reaction can preferably be carried out in a solvent at a temperature ranging from 0° C. to a boiling point of the solvent used. Preferred solvents used in this reaction are benzene, toluene, xylene, acetone, tetrahydrofuran, chloroform, dichloroethane, dioxane, dimethylsulfoxide and a mixture thereof.

For the production of the compounds of the present invention, some other methods can also be applied. Examples of such methods are those disclosed in U.S. Pat. No. 3,511,836.

The compounds obtained as mentioned above may easily be converted into pharmaceutically acceptable salts form by treating with acids such as hydrochloric acid, sulfuric acid, nitric acid, phosphoric acid, formic acid, acetic acid, citric acid, malic acid, succinic acid, malonic acid, lactic acid, maleic acid, salicylic acid, p-toluenesulfonic acid and the like.

The compounds [I] of the present invention and their non-toxic salts can be administered parenterally or orally with dosage adjusted to individual requirements (0.1–200 mg/human body (60 kg of body weight)/day) in the form of conventional pharmaceutical preparations. For instance, they may be administered in the form of a conventional solid pharmaceutical preparation such as tablets or capsules or in the form of a conventional liquid pharmaceutical preparation such as suspensions, emulsions or solutions.

The following examples are given to illustrate the present invention more precisely, but it is not intended to limit the present invention thereto.

EXAMPLE 1

A mixture of 2-chloro-4-amino-6,7-dimethoxyquinazoline (2.4 g), 1-(1-adamantanecarbonyl)piperazine (2.5 g) and n-butanol (60 ml) was refluxed for 10 hours. After cooling, the solvent was evaporated under reduced pressure, and water was added to the residue. After treating with aqueous ammonia, the precipitated crystals were collected to give crude 2-{4-(1-adamantanecarbonyl)-1-piperazinyl}-4-amino-6,7-dimethoxyquinazoline, m.p. 237°–240° C. Recrystallization from methanol gave pure 2-{4-(1-adamantanecarbonyl)-1-piperazinyl}-4-amino-6,7-dimethoxyquinazoline, m.p. 242°–243° C.

EXAMPLE 2

To a mixture of 2-piperazino-4-amino-6,7-dimethoxyquinazoline (1 g), chloroform (50 ml) and triethylamine (0.42 g), was gradually added 1-adamantanecarbonyl chloride (0.83 g). The almost dissolved mixture was heated at 45°–50° C. for 2 hours. After cooling, the mixture was washed with water, dried over anhydrous sodium sulfate and evaporated under reduced pressure to give 2-{4-(1-adamantanecarbonyl)-1-piperazinyl}-4-amino-6,7-dimethoxyquinazoline, m.p. 240°–242° C.

The following compounds were also prepared by the same procedures as mentioned in Example 1:

4-Amino-6,7-dimethoxy-2-[4-{3-oxatricyclo[4,2,1,0$^{4,8}$]nonane-1-carbonyl}-1-piperazinyl]quinazoline, m.p. 277°–279° C.

4-Amino-6,7-dimethoxy-2-[4-{3-oxatricyclo[4,3,1,0$^{4,9}$]decane-1-carbonyl}-1-piperazinyl]quinazoline, m.p. 294°–295° C.

4-Amino-6,7-dimethoxy-2-[4-{3-oxatricyclo[4,2,1,0$^{4,8}$]nonane-9-carbonyl}-1-piperazinyl]quinazoline, m.p.

4-Amino-2-[4-{bicyclo[2,2,1]hept-2-ene-5-carbonyl}-1-piperazinyl]-6,7-dimethoxyquinazoline, m.p. 199°–200° C.

What is claimed is:

1. A compound of the formula:

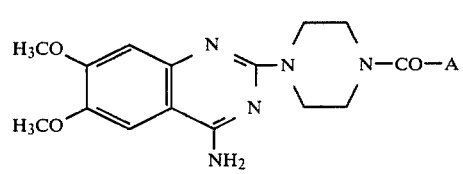

wherein A is

wherein n is an integer of 1 or 2, or

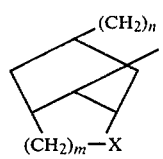

wherein X is O or $CH_2$, and n and m are independently an integer of 1 or 2, and its non-toxic pharmaceutically acceptable salts.

2. A compound according to claim 1, which is represented by the formula:

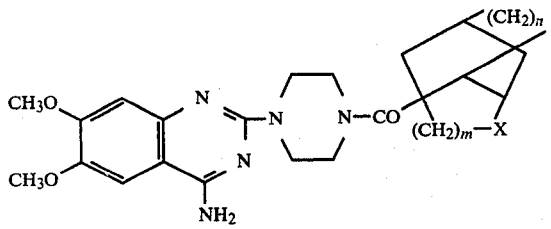

wherein X is a methylene group or an oxygen atom, m is 1 or 2 and n is 1 or 2, and its pharmaceutically acceptable salts.

3. A compound according to claim 1, which is represented by the formula:

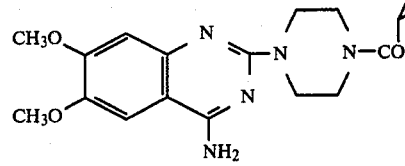

wherein n is 1 or 2, and its pharmaceutically acceptable salts.

4. 2-{4-(1-Adamantanecarbonyl)-1-piperazinyl}-4-amino-6,7-dimethoxyquinazoline, and its pharmaceutically acceptable salts.

5. 4-Amino-6,7-dimethoxy-2-[4-{3-oxatricyclo[4,2,1,0$^{4,8}$]nonane-1-carbonyl}-1-piperazinyl]-quinazoline, and its pharmaceutically acceptable salts.

6. 4-Amino-6,7-dimethoxy-2-[4-{3-oxatricyclo[4,3,1,0$^{4,9}$]decane-1-carbonyl}-1-piperazinyl]-quinazoline, and its pharmaceutically acceptable salts.

7. 4-Amino-6,7-dimethoxy-2-[4-{3-oxatricyclo[4,2,1,0$^{4,8}$]nonane-9-carbonyl}-1-piperazinyl]-quinazoline, and its pharmaceutically acceptable salts.

8. 4-Amino-2-[4-{bicyclo[2,2,1[hept-2-ene-5-carbonyl}-1-piperazinyl]-6,7-dimethoxyquinazoline, and its pharmaceutically acceptable salts.

9. An antihypertensive composition comprising a compound as claimed in claim 1 or its pharmaceutically acceptable salts in an antihypertensively-effective amount, and a pharmaceutically acceptable carrier.

* * * * *